(12) United States Patent
Hosoi et al.

(10) Patent No.: US 9,245,660 B2
(45) Date of Patent: Jan. 26, 2016

(54) ELECTROCONDUCTIVE PARTICLE AND METAL PASTE, AND ELECTRODE

(71) Applicant: TANAKA KIKINZOKU KOGYO K.K., Tokyo (JP)

(72) Inventors: Takuya Hosoi, Kanagawa (JP); Nobuhisa Okamoto, Kanagawa (JP); Koichi Sakairi, Kanagawa (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 171 days.

(21) Appl. No.: 14/238,200

(22) PCT Filed: Sep. 25, 2012

(86) PCT No.: PCT/JP2012/074469
§ 371 (c)(1),
(2) Date: Feb. 10, 2014

(87) PCT Pub. No.: WO2013/047465
PCT Pub. Date: Apr. 4, 2013

(65) Prior Publication Data
US 2014/0203224 A1    Jul. 24, 2014

(30) Foreign Application Priority Data

Sep. 27, 2011   (JP) ................. 2011-210381

(51) Int. Cl.
| | |
|---|---|
| H01B 1/02 | (2006.01) |
| H01B 1/08 | (2006.01) |
| H01B 1/16 | (2006.01) |
| H01B 1/22 | (2006.01) |
| C04B 35/10 | (2006.01) |
| C04B 35/48 | (2006.01) |
| C04B 35/74 | (2006.01) |
| C04B 35/622 | (2006.01) |

(52) U.S. Cl.
CPC .. *H01B 1/02* (2013.01); *H01B 1/08* (2013.01); *H01B 1/16* (2013.01); *H01B 1/22* (2013.01); *C04B 35/10* (2013.01); *C04B 35/48* (2013.01); *C04B 35/622* (2013.01); *C04B 35/74* (2013.01)

(58) Field of Classification Search
None
See application file for complete search history.

(56) References Cited

U.S. PATENT DOCUMENTS

| | | | | |
|---|---|---|---|---|
| 4,002,503 A | * | 1/1977 | Bourne | ..................... C22F 1/14 148/514 |
| 6,841,121 B2 | * | 1/2005 | Shoji | ..................... C03B 5/1672 419/19 |
| 2005/0065026 A1 | * | 3/2005 | Okubo | ..................... B01J 23/63 502/339 |
| 2007/0128439 A1 | * | 6/2007 | Kim | ......................... B01J 13/02 428/404 |
| 2012/0126183 A1 | | 5/2012 | Hosoi et al. | |

FOREIGN PATENT DOCUMENTS

| | | |
|---|---|---|
| JP | H 1026603 A | 1/1998 |
| JP | 3510050 B2 | 3/2004 |
| JP | 2006-193796 A | 7/2006 |
| JP | 2006193796 A * | 7/2006 |
| JP | 2006-302848 A | 11/2006 |
| JP | 2006-310340 A | 11/2006 |
| JP | 2011-162879 A | 8/2011 |
| JP | 4834170 B1 | 12/2011 |

OTHER PUBLICATIONS

English text machine translation of Asaki et al. (JP 2006193796 A), accessed from the AIPN website, attached as a PDF.*

* cited by examiner

*Primary Examiner* — Harold Pyon
*Assistant Examiner* — Katie L Hammer
(74) *Attorney, Agent, or Firm* — Roberts & Roberts, LLP

(57) ABSTRACT

The present invention is an electroconductive particle for forming an electrode including a precious metal particle including Pt or a Pt alloy and having an average particle diameter of 50 to 150 nm, a first ceramic particle including $Al_2O_3$ or $ZrO_2$ dispersed in the precious metal particle and having an average particle diameter of 5 to 50 nm, and a second ceramic particle including $Al_2O_3$ or $ZrO_2$ bonded to an outer periphery of the precious metal particle and having an average particle diameter of 5 to 50 nm. The sum of the volume of the first ceramic particle and the volume of the second ceramic particle is preferably 2 to 40 vol % based on the whole electroconductive particle. A metal paste containing the electroconductive particle according to the invention is one from which an electrode film of low resistance and excellent durability can be manufactured and further excellent in adherence and conformability to a substrate.

20 Claims, No Drawings

ELECTROCONDUCTIVE PARTICLE AND METAL PASTE, AND ELECTRODE

BACKGROUND OF THE INVENTION

1. Field of the Invention

The present invention relates to an electroconductive, particle to form various types of electrodes such as sensor electrodes, heater electrodes and lead wire electrodes, and further to a metal paste for forming an electrode using the electroconductive particle.

2. Description of the Related Art

In manufacture of sensor electrodes of various types of gas sensors such as oxygen sensors, NOx sensors and exhaust gas temperature sensors, heater electrodes and the like, the manufacture is carried out generally by applying a metal paste containing an electroconductive metal powder on a substrate by one of various types of methods such as screen printing and firing the applied metal paste. A form of a metal paste is often used because the metal paste form is preferable from the viewpoint that the form can cope with a complicated pattern of an electrode, and besides from the viewpoint of the manufacturing efficiency in which a substrate and an electrode can simultaneously be manufactured by application and firing of a metal paste on a green sheet for forming a ceramic substrate.

As a metal paste for forming an electrode, a metal paste is conventionally used in which an electroconductive particle such as a precious metal and a ceramic powder such as $Al_2O_3$ or $ZrO_2$ are mixed in a solvent. Mixing a ceramic powder in a metal paste, when a substrate and an electrode are manufactured by application and firing of a metal paste on a green sheet as described above, is for improving the adherence of the electrode by correcting a difference in contraction rate between the metal paste and the green sheet and eliminating the problem of warpage and deformation of the substrate due to the contraction rate difference. Further, mixing a ceramic powder in a metal paste also exhibits an advantage of being capable of preventing oversintering of the electroconductive particle in firing.

However, a ceramic powder, while securing formability of an electrode film as described above, raises the resistance value of the manufactured electrode film, and is likely to make the resistance value considerably higher than in an electrode of a bulk metal. Therefore, the use of a ceramic powder is not preferable from the viewpoint of the property as a precursor material of an electrode, however if no ceramic or a too small amount thereof is mixed, the formation itself of an electrode becomes impossible, and thereby there has been no choice but to mix a ceramic as an actual situation.

The significance of mixing a ceramic powder in a metal paste for forming an electrode has also an aspect of securing the durability of an electrode film. The durability of an electrode is a property required, for example, in an electrode film exposed to a high temperature of a heater electrode or the like, and an electrode film having poor durability has a risk of causing wire breakage in a relatively short time. Then, although the durability of an electrode film can be improved by an increase in the amount of a ceramic powder mixed, there is a demand of reducing the amount of the ceramic powder mixed from the viewpoint of the reduction of the resistance value, as described above.

PRIOR ART DOCUMENTS

Patent Literature

Patent Literature 1: Japanese Patent No. 3510050

SUMMARY OF THE INVENTION

Problems to be Solved by the Invention

The present invention takes the above-mentioned situation into consideration, and provides an electroconductive particle constituting a metal paste from which an electrode film of low resistance and excellent durability can be manufactured and excellent in adherence and conformability to a substrate. The present invention also has an object to provide a metal paste utilizing such an electroconductive particle.

Means for Solving the Problems

The present inventors first studied a firing process when a conventional metal paste is made into an electrode film. The conventional metal paste is in a state that electroconductive particles and ceramic particles are individually dispersed in a solvent, and is fired to sinter and bond the electroconductive particles to thereby secure continuity as an electrode, but sintering of the ceramic powder is also caused in the firing of the metal paste. Here, since there is a difference in temperature between the sintering temperature of the electroconductive particles (metal) and the sintering temperature of the ceramic powder, and the sintering temperature of the electroconductive particles is lower, sintering of the electroconductive particles is caused preferentially in the sintering process. Therefore, unsintered ceramic particles in the vicinity of the electroconductive particles aggregate as if being pushed out from the electroconductive particles starting being sintered first. That is, the conventional metal paste causes a state that the electroconductive particles and the ceramic particles are inhomogeneously dispersed in the sintering process. Then, if sintering of the ceramic progresses in such an inhomogeneous state, the ceramic particles become resultantly coarse.

The present inventors deemed that the coarsening of a ceramic particle as described above is a factor of raising the resistance of an electrode film. Such coarsening of a ceramic particle will more likely to happen when the amount of the ceramic powder mixed is increased. It is true, but a ceramic powder is necessary for securing adherence of an electrode, and completely excluding the ceramic powder from a metal paste is not deemed to be a preferable measure. Then, the present inventors have studied to find a metal paste containing ceramic particles in a fine state also after being fired.

As a result of the study, the present inventors have conceived not such a constitution of a metal paste in which an electroconductive particle and a ceramic powder are separately dispersed in a solvent as in conventional metal pastes, but a constitution in which the ceramic is bonded to the electroconductive particle and the resultant is dispersed in a solvent. The present inventors have thus found that the fine ceramic particles are dispersed in the electroconductive particles as a bonding state of the ceramic to the electroconductive particle.

The present invention to solve the above-mentioned problem is an electroconductive particle for forming an electrode which comprises a precious metal particle comprising Pt or a Pt alloy and having an average particle diameter of 50 to 150 nm, a first ceramic particle comprising $Al_2O_3$ or $ZrO_2$ dispersed in the precious metal particle and having an average particle diameter of 5 to 50 nm, and a second ceramic particle comprising $Al_2O_3$ or $ZrO_2$ bonded to an outer periphery of the precious metal particle and having an average particle diameter of 5 to 50 nm.

The present invention discloses an electroconductive particle in a pre-stage to be made into a paste, and is an electroconductive particle in which a precious metal particle and a ceramic particle are bonded, and the ceramic particle as a dispersed particle is dispersed in the precious metal particle as a matrix. The precious metal particle according to the present invention is in a state that the whole ceramic particles are in a state of being completely confined in the interior of the precious metal particle. In a metal paste using the present invention, although preferential sintering of a precious metal particle, having a low sintering temperature, is caused in the sintering process, no movement of a ceramic particle is caused in this stage, and the state is maintained as it is until the completion of the sintering of the precious metal particle. Therefore, the ceramic particle in the precious metal particle is in a fine state also in an electrode film, and never makes a factor of raising the resistance value. Such a fine ceramic particle further has a function as a dispersion-strengthening material of the electrode film, and resultantly boosts the durability.

In the electroconductive particle according to the present invention, ceramic particles are dispersed in the interior of a precious metal particle, and ceramic particles are simultaneously bonded to (carried on) a periphery of the precious metal particle. The significance that ceramic particles are carried on a periphery of the precious metal particle lies in complement of the amount of the ceramic in the electroconductive particle interior. Also in the present invention, the ceramic particles dispersed in the precious metal particle interior has a function of improvement of adherence with a substrate and other functions as in conventional technologies. It is true, but incorporation of the ceramic particles in an enough amount to sufficiently exhibit the above-mentioned action in the interior of the fine precious metal particle is difficult, and the formation of an electrode may possibly become difficult with the state as it is. Then, complementary bonding of ceramic particles on a periphery of a precious metal particle can secure the ceramic particles in an enough amount to secure formability. The ceramic particles on a periphery of the precious metal particle, since being in a bonding state with the precious metal particle, can move together with the precious metal particle also in the sintering process of a metal paste. Therefore, there is no risk that ceramic particles individually dispersed are sintered and coarsened, as in conventional technologies. In the present invention, although more or less sintering is caused, coarsening is hardly caused to such a degree that the resistance value is excessively raised.

As described above, in the electroconductive particle according to the present invention, dispersing ceramic particles in the interior of a precious metal particle prevents coarsening of the ceramic particles when an electrode film is made to thereby reduce the resistance value of the electroconductive particle, and improves the durability of the electroconductive particle by dispersion-strengthening of the fine ceramic particles. Further in order to secure formability of an electrode film, ceramic particles are bonded on a periphery of a precious metal particle to complement the ceramic particles in a form of not raising the resistance value.

Hereinafter, the present invention will be described in more detail. In an electroconductive particle according to the present application, a precious metal particle comprises Pt or a Pt alloy. These metals are good in electroconductivity and also excellent in heat resistance. Since among various types of sensors, there are those used at high temperatures as in exhaust gas sensors for automobiles, these metals are suitable as an electrode material thereof. Which one is used between Pt and a Pt alloy as a precious metal particle can be chosen according to the application and required properties. Pt is lower in the resistance than a Pt alloy, and is suitable for applications, such as sensor electrodes and lead wire electrodes, requiring low resistance firstly. By contrast, a Pt alloy is rather higher in the resistance than Pt, but the Pt alloy is low in the resistance temperature coefficient (TCR), and is suitable for applications such as heater electrodes. Here, a metal to be alloyed with Pt as a Pt alloy is preferably Pd, Au, Ag and Rh. A Pt—Pd alloy, which contains Pd, is preferable because of having good affinity for a ceramic to become a substrate, and also from a point that wettability is good when the alloy is made into a paste. Here, the content of Pd in a Pt—Pd alloy is preferably made to be 30 wt % or lower. This is because if the content of Pd is excessively high, a Pd oxide is liable to deposit in the firing process, and the reliability of an electrode resultantly decreases.

The average particle diameter of a precious metal particle is made to be 50 to 150 nm. Particles having as a too fine diameter as smaller than 50 nm makes it difficult for a thick electrode film to be manufactured. By contrast, the case exceeding 150 nm is not preferable because the dispersibility when the particles are made into a metal paste falls.

A ceramic particle (first ceramic particle) dispersed in a precious metal particle comprises a ceramic of $Al_2O_3$ or $ZrO_2$. This is a result of joinability to a ceramic substrate being taken into consideration. The average particle diameter of the ceramic particle is made to be 5 to 50 nm. The case of smaller than 5 nm is not preferable because there arises an apprehension that the sintering temperature decreases due to an influence of the size effect; and ceramic particles exceeding 50 nm is not preferable because the dispersibility thereof in a precious metal particle falls and the dispersion-strengthening cannot be anticipated.

On the other hand, a ceramic particle (second ceramic particle) to be bonded on an outer periphery of the precious metal particle comprises $Al_2O_3$ or $ZrO_2$ as in the ceramic particle dispersed in the interior of the precious metal particle, and the average particle diameter thereof is made to be 5 to 50 nm. The average particle diameter of smaller than 5 nm is not preferable because there arises an apprehension of the sintering temperature falling as in the above. Although the ceramic particle to be bonded on an outer periphery of a precious metal particle is not anticipated to provide dispersion-strengthening, the average particle diameter exceeding 50 nm is not preferable because there arises an apprehension of coarsening by sintering.

In any case, $Al_2O_3$ generally distributed and having a purity of 90 wt % or higher is preferable; and $ZrO_2$ usable is pure zirconia and besides a stabilized zirconia in which several percent of oxides such as yttria and calcia is added. Here, in addition to $Al_2O_3$ or $ZrO_2$, oxides of hafnium, cerium, titanium, tantalum, magnesium and the like can act as the ceramic particle of the present invention. However, in consideration of ease of material procurement, cost and the like, $Al_2O_3$ or $ZrO_2$ is preferable.

The total amount of a ceramic particle contained in the electroconductive particle according to the present invention, that is, the sum of the amount of the ceramic particle dispersed in a precious metal particle and the amount of the ceramic particle carried on a periphery of the precious metal particle is preferably 2 to 40 vol % based on the whole electroconductive particle. This is because with the total amount of smaller than 2 vol %, securing of the adherence to a substrate, which is the reason for using a ceramic particle, and the like become difficult, and exfoliation from the substrate and deformation of a metal paste is likely to happen when the metal paste is fired. This is also because with the total amount exceeding 40 vol %, even in consideration of an effect of suppressing coarsening of ceramic particles in the present invention, the resistance value of an electrode film becomes excessively high, and the electroconductivity cannot be provided. Here, a preferable range of the total amount of the ceramic particle is 5.0 to 35 vol %.

Here, the amount of a ceramic particle dispersed in a precious metal particle is preferably made to be 0.5 to 15 vol % based on the whole electroconductive particle. This is because with the amount of smaller than 0.5 vol %, the degree of dispersion in an electrode film after being fired is low and an effect of improving the durability cannot sufficiently be exhibited. This is also because with the amount exceeding 15 vol %, the resistance is raised. A more preferable amount of the ceramic particle dispersed in the precious metal particle is 1.0 to 12 vol %.

Then, a method for manufacturing an electroconductive particle according to the present application will be described. An electroconductive particle according to the present application has a constitution in which a ceramic, that is, a metal oxide is dispersed in a precious metal as a matrix. As a method for manufacturing such a metal material in which an oxide is dispersed, although an internal oxidation method is generally known, the internal oxidation method cannot be used in order to disperse an oxide in a precious metal fine particle as a matrix as in the present invention. The internal oxidation method is a method in which an alloy of a metal to become a matrix and a metal to become a metal source of an oxide to be dispersed is heated in an oxidizing atmosphere, but in the case where such means is applied to a fine particle as in the present invention, the oxide segregates and deposits on the powder surface, and the oxide is hardly held in a dispersed state in the powder interior.

The present inventors have found that: a composite particle having a core/shell structure composed of a precious metal particle and a shell-like ceramic covering at least a part of the precious metal particle is manufactured and subjected to a heat treatment; thereby, bonds among the precious metal particles of the composite particles are generated and the shell-like ceramic infiltrates and disperses finely in the precious metal particle at the same time. Then, the present inventors have found a method for manufacturing an electroconductive particle according to the present application by utilizing this phenomenon. That is, a method for manufacturing an electroconductive particle according to the present application involves manufacturing a composite particle having a core/shell structure composed of a precious metal particle comprising Pt or a Pt alloy and a shell-like ceramic covering at least a part of the precious metal particle and containing $Al_2O_3$ or $ZrO_2$, and thereafter heating the composite particle at 650 to 1,200° C.

Here, a composite particle having a core/shell structure being a precursor of an electroconductive particle according to the present application preferably has an average particle diameter of 30 to 100 nm. The heat treatment for forming dispersed particles is for causing bonding and granulation of precious metal particles and for making the particle diameter of electroconductive particles to be manufactured to be in a reasonable range. The amount of the shell-like ceramic of the composite particle covering the precious metal particle is preferably 2 to 40 vol % based on the whole composite particle. This is also for making the amount of the ceramic in the electroconductive particle to be manufactured to be in a reasonable range.

Manufacture of a composite particle having a core/shell structure can utilize a gas-phase reaction in a high-temperature atmosphere. This method involves mixing a metal or alloy powder to become a precious metal particle and a ceramic powder to become a shell, discharging the mixed powder into an atmosphere of a high temperature equal to or higher than boiling points of both the components, cooling the discharged mixed powder, and recovering the fine powder produced. At this time, the high-temperature atmosphere to discharge the powders as raw materials is preferably by a plasma atmosphere. The amount of the ceramic can be set by regulation of the ratio thereof in the mixed powder in the stage of manufacturing the composite particle.

The reason that the heat treatment temperature of a composite particle is made to be 650 to 1,200° C. is because with the temperature of lower than 650° C., bonds of precious metal particles are hardly generated, and consequently, an electroconductive particle cannot be manufactured. The reason is also because with the temperature exceeding 1,200° C., an electroconductive particle is coarsened, which is therefore not preferable. Here, in the heat treatment, the heating time is preferably 0.5 to 10.0 hours.

A metal paste using the electroconductive particle according to the present invention is one obtained by mixing of the electroconductive particle and a solvent. In the present invention, mixing of a ceramic powder (frit) essential as a constitution of conventional metal pastes is not essential. Solvents usable for manufacture of a metal paste in the present invention are usual ones such as ethylene glycol, propylene glycol, ethyl cellosolve, butyl cellosolve, ethylene glycol monophenyl ether, ethylene glycol monomethyl ether acetate, benzyl alcohol, kerosene, paraffin, toluene, cyclohexanone, γ-butyrolactone, methyl ethyl ketone, N-methylpyrrolidone, N-dimethylformamide, N-methylacetoamide, N,N-dimethylacetoamide, butyl carbitol, turpentine oil, α-terpineol, terbineol, and the like, and a solvent such as α-terpineol is suitable.

The amount of an electroconductive particle mixed is preferably 4.0 to 40 vol % with respect to the whole paste. This is because with the amount mixed of smaller than 4.0 vol %, an electrode film becomes too thin, and with the amount mixed exceeding 40 vol %, making the electroconductive particle into a paste becomes difficult.

A resin usually used may further be added to a metal paste in order to make the metal paste have viscosity and thixotropy. The resin is usually natural resins, amino-based resins, alkyd resins and the like. Particularly a resin such as ethyl cellulose is suitable.

In the case where an electrode is manufactured with the paste for forming an electrode, the firing temperature is preferably 1,300 to 1,600° C. This is because the electrode having a low resistance value can be obtained by sufficient sintering. An electrode film thus formed is in a state that fine ceramic particles ($Al_2O_3$ particles, $ZrO_2$ particles) are dispersed, and specifically, half or more of ceramic particles are ones of 300 nm or smaller.

Advantageous Effects of the Invention

As described hitherto, the electroconductive particle according to the present invention is applied to a metal paste, and fired, thereby an electrode film can be formed which has fine ceramic particles dispersed therein and has a low resistance and an excellent durability. The metal paste according to the present invention can be adapted to any electrode film of thick films and thin films, since the resistance reduction allows the film thickness reduction of an electrode film having the same durability as conventional films, the metal paste leads to the reduction of the amount of a precious metal such as Pt to be used and the cost reduction of electronic devices.

DETAILED DESCRIPTION OF THE PREFERRED EMBODIMENTS

First Embodiment

Hereinafter, an embodiment according to the present invention will be described. An electroconductive particle was manufactured in which $Al_2O_3$ as a ceramic particle was dispersed in and carried on Pt as a precious metal particle, and made into a metal paste and fired to thereby obtain an electrode, and the electrode was measured for the resistance value. The durability of the electrode film was also evaluated.

(A) Manufacture of an Electroconductive Particle (i) Manufacture of a Composite Particle A Pt powder of 10 nm in average particle diameter and an $Al_2O_3$ powder of 10 nm in average particle diameter were mixed by means of a V-type mixer to thereby prepare a homogeneous mixed powder (the amount of the ceramic to the whole mixed powder was 15 vol %). The mixing ratio at this time corresponds to an amount of an $Al_2O_3$ shell of a composite particle powder added. Then, the mixed powder was discharged in a plasma atmosphere in an argon atmosphere in a high-frequency induction thermal plasma apparatus. A fine powder generated was recovered with a filter. By the above step, a composite particle powder was obtained which had a core/shell structure of Pt as a precious metal particle and $Al_2O_3$ as a shell. For the composite particle powder at this time, the size (maximum size) of the particle was read from a TEM photograph, and the particle diameter of the precious metal particle was 25 nm and the particle diameter of the whole composite particle was 30 nm.

(ii) Manufacture (Heat Treatment) of an Electroconductive Particle

The composite particle powder of a core/shell structure manufactured in the above was subjected to a heat treatment to thereby manufacture an electroconductive particle. The heat treatment temperature was set at 950° C. and the heat treatment time was set to be 1 hour. This heat treatment manufactured the electroconductive particle in which $Al_2O_3$ particles were dispersed in a Pt particle, and $Al_2O_3$ particles were carried on an outer periphery of the Pt particle. The electroconductive particle was observed for the cross-section by SEM, and the average particle diameter of the Pt particle was calculated to be 100 nm; the average particle diameter of the $Al_2O_3$ particle on an outer periphery of the Pt particle, to be 25 nm; and the average particle diameter of the $Al_2O_3$ particle dispersed in the interior of the Pt particle, to be 15 nm. The content of the $Al_2O_3$ particle dispersed in the Pt particle was calculated to be 1.5 vol % from the areal conversion of the cross-section.

(B) Fabrication of a Paste for Forming an Electrode

The electroconductive particle manufactured in the above was charged in an ester alcohol as an organic solvent; a diamine-based surfactant and ethyl cellulose were further mixed; and the mixture was mixed and kneaded by means of a three-roll mill to thereby make a paste. The amount of the electroconductive particle mixed was made to be 25 vol %.

(C) Fabrication of an Electrode

The metal paste manufactured in the above was applied with screen printing on a 99-wt % alumina green sheet. The applied metal paste was thereafter dried at 80° C. for 20 min, and subjected to a firing treatment at 1,500° C. for 1 hour to thereby fabricate an electrode film (film thickness: 15 μm).

In addition to the above, electroconductive particles were manufactured by being varied in the amount of the ceramic, and electrode films were manufactured therefrom. A method for manufacturing the electroconductive particles was basically the same as in the above, and composite particle powders were obtained by being varied in the amount of the $Al_2O_3$ powder mixed together with the Pt powder by the gas-phase reaction method. Then, the composite particle powders were subjected to a heat treatment to thereby manufacture electroconductive particles. Then, metal pastes were manufactured and electrodes were manufactured, as in the above.

Metal pastes as conventional ones having a Pt powder and a ceramic powder separately mixed were further manufactured (Conventional Examples 1 to 3). A Pt powder of 0.7 μm in particle diameter as the Pt powder and an $Al_2O_3$ powder of 0.3 μm in particle diameter as the ceramic powder were used, and the same solvent and other components as in the above were used; and metal pastes were manufactured by being varied in the amount of the ceramic mixed, and electrodes were fabricated.

The electrode films manufactured during the above-mentioned step were measured for resistance values with a digital multimeter by a 4-terminal method. An endurance test to evaluate the durability of the electrodes was carried out. The endurance test was carried out by energizing an electrode on a substrate to thereby heat the substrate to 1,200° C., and by measuring the time until wire breakage occurred. These test results are shown in Table 1.

TABLE 1

| | $Al_2O_3$ Amount | Resistance Value (mΩ/□/10 μm) | | Endurance Test (h) |
| --- | --- | --- | --- | --- |
| | | Room temperature | 1000° C. | |
| Example 1 | 5 vol % | 19 | 75 | 290 |
| Example 2 | 15 vol % | 22 | 86 | 652 |
| Example 3 | 20 vol % | 32 | 126 | 380 |
| Example 4 | 40 vol % | 120 | 471 | 298 |
| Comparative Example 1 | 45 vol % | ∞ | ∞ | — |
| Conventional Example 1 | 5 vol % | 18 | 71 | 50 |
| Conventional Example 2 | 15 vol % | 24 | 94 | 74 |
| Conventional Example 3 | 40 vol % | 43 | 169 | 220 |

∞: Unmeasurable due to excessive resistance value (endurance test was not carried out)

It is clear from the Table that an electrode film fabricated from a metal paste using an electroconductive particle according to each Example is much more improved in high-temperature durability than an electrode film manufactured from a conventional metal paste in the case of the same amount of the ceramic, and exhibits an endurance time several times the conventional technology. This means that in the case where the amount of the ceramic is specified based on the durability, for example, even if a conventional electrode film requiring 40 vol % of a ceramic (Conventional Example 3) is replaced by an electrode film reduced in the amount of the ceramic to 5 vol % (Example 1), the electrode film of Example 1 exhibits sufficient durability and further exhibits a lower resistance value.

Second Embodiment

Here, electroconductive particles using a Pt—Pd alloy (Pd: 25 wt %) as a precious metal particle were manufactured. A manufacture method was basically the same as in First Embodiment, and composite particle powders of a core/shell structure having the Pt—Pd alloy as the precious metal particle and $Al_2O_3$ as the shell were obtained with a Pt—Pd alloy powder (average particle diameter: 10 nm) as the raw material powder instead of the Pt powder under the same other conditions as in First Embodiment by the gas-phase reaction method. Then, the composite particle powders were subjected to a heat treatment (the heat treatment temperature was 950° C., and the heat treatment time was 1 hour) to thereby manufacture electroconductive particles. This heat treatment manufactured the electroconductive particles in which $Al_2O_3$ particles were dispersed in the interior of and carried on an outer periphery of Pt—Pd particles as a precious metal particle. Then, with the electroconductive particles, metal pastes were manufactured and electrodes (the film thickness of the electrode film was 15 μm) were fabricated, as in First Embodiment. For comparison to these, a metal paste as a conventional one having a Pt—Pd alloy powder and a ceramic powder separately mixed was manufactured (Conventional Example 4). Then, the resistance value measurement and the endurance test were carried out on the each electrode film. The test results are shown in Table 2.

TABLE 2

|  | $Al_2O_3$ Amount | Resistance Value (mΩ/□/10 μm) | | Endurance Test (h) |
| --- | --- | --- | --- | --- |
|  |  | Room temperature | 1000° C. |  |
| Example 5 | 4 vol % | 30 | 56 | 250 |
| Example 6 | 12 vol % | 42 | 79 | 624 |
| Example 7 | 20 vol % | 53 | 100 | 586 |
| Example 8 | 25 vol % | 74 | 139 | 300 |
| Example 9 | 34 vol % | 92 | 173 | 290 |
| Conventional Example 4 | 20 vol % | 50 | 94 | 150 |

It is clear from Table 2 that with respect to the effect of the reduction of the resistance value and the improvement of the durability, even use of a Pt—Pd alloy as the precious metal particle has the same tendency as in First Embodiment.

Third Embodiment

Here, an electroconductive particle using $ZrO_2$ (YSZ) as the ceramic particle was manufactured in place of the electroconductive particle of First Embodiment. A manufacture method thereof basically used the same condition as in First Embodiment, and a mixed powder of a Pt powder and a $ZrO_2$ (YSZ) powder was discharged into a plasma gas phase to thereby manufacture a composite particle powder of a core/shell structure. Then, the composite particle powder was subjected to a heat treatment as in First Embodiment to thereby manufacture an electroconductive particle. Then, a metal paste was manufactured, and applied and fired on a zirconia green sheet to thereby make an electrode film, and the electrode film was measured for the resistance value. For comparison, electrode films of metal pastes having a Pt powder and a $ZrO_2$ (YSZ) powder separately mixed were evaluated for properties thereof (Conventional Examples 5 and 6). The results are shown in Table 3.

TABLE 3

|  | $ZrO_2$ Amount | Resistance Value (mΩ/□/10 μm) | | Endurance Test (h) |
| --- | --- | --- | --- | --- |
|  |  | Room temperature | 1000° C. |  |
| Example 10 | 10 vol % | 18 | 74 | 420 |
| Example 11 | 35 vol % | 31 | 122 | 300 |

TABLE 3-continued

|  | $ZrO_2$ Amount | Resistance Value (mΩ/□/10 μm) | | Endurance Test (h) |
| --- | --- | --- | --- | --- |
|  |  | Room temperature | 1000° C. |  |
| Conventional Example 5 | 10 vol % | 19 | 75 | 70 |
| Conventional Example 6 | 35 vol % | 40 | 157 | 205 |

It is clear from the Table that electroconductive particles using $ZrO_2$ (YSZ) as the ceramic particle were also recognized to be more improved in the durability than metal pastes of the Conventional Examples.

Fourth Embodiment

Here, studies were made to clarify the lower limit value of the amount of the ceramic (total amount) in an electroconductive particle. Manufacture of electroconductive particles was the same as in First Embodiment, and the adjustment of the amount of the ceramic was carried out by adjusting the amount of an $Al_2O_3$ powder in a mixed powder. Then, the electroconductive particles and metal pastes were manufactured as in First Embodiment, and applied and fired in three patterns of 0.5×20 mm (three lines at 1-mm intervals), 0.1× 5.0 mm (11 lines at 0.1 to 0.5-mm intervals) and 5×5 mm, on an alumina sheet. After the firing, the presence/absence of exfoliation and warpage of the electrode films was visually checked. The results are shown in Table 4.

TABLE 4

| $Al_2O_3$ Amount | Warpage | Exfoliation |
| --- | --- | --- |
| 10 vol % | Excellent | Excellent |
| 5 vol % | Excellent | Excellent |
| 2 vol % | Good | Excellent |
| 1.5 vol % | Good | Poor |
| 1.0 vol % | Poor | Poor |

Excellent . . . there occurred no warpage and exfoliation
Good . . . there occurred almost no warpage and exfoliation, but warpage and exfoliation started to partially occur
Poor . . . there clearly occurred warpage and exfoliation It is clear from Table 4 that in the case where the amount of the ceramic is small, exfoliation and deformation are liable to be caused after the firing. Then, it can be confirmed that the practically acceptable amount of the ceramic has a lower limit of 2 vol %. Here, the above results used $Al_2O_3$ as the ceramic, but the case of using $ZrO_2$ gave similar results.

INDUSTRIAL APPLICABILITY

The present invention can provide a paste for forming an electrode capable of forming a low-resistance electrode. An electrode manufactured by the present invention is excellent also in durability.

What is claimed is:
1. An electroconductive particle for forming an electrode, comprising: a precious metal particle comprising Pt or a Pt alloy and having an average particle diameter of 50 to 150 nm; a first ceramic particle comprising $Al_2O_3$ or $ZrO_2$ dispersed in the interior of the precious metal particle and having an average particle diameter of 5 to 50 nm; and a second ceramic particle comprising $Al_2O_3$ or $ZrO_2$ bonded to an outer periphery of the precious metal particle and having an average particle diameter of 5 to 50 nm.

2. The electroconductive particle for forming an electrode according to claim 1, wherein a sum of a volume of the first ceramic particle and a volume of the second ceramic particle is 2 to 40 vol % based on the whole electroconductive particle.

3. The electroconductive particle for forming an electrode according to claim 1, wherein a volume of the first ceramic particle dispersed in the precious metal particle is 0.5 to 15 vol % based on the whole electroconductive particle.

4. The electroconductive particle for forming an electrode according to claim 1, wherein the precious metal particle is Pt.

5. The electroconductive particle for forming an electrode according to claim 1, wherein the precious metal particle is a Pt—Pd alloy containing 30 wt % or less of Pd.

6. A method for manufacturing an electroconductive particle for forming an electrode, said electroconductive particle defined in claim 1, comprising:
   manufacturing a composite particle having a core/shell structure composed of a precious metal particle comprising Pt or a Pt alloy and a shell-like ceramic covering at least a part of the precious metal particle and comprising $Al_2O_3$ or $ZrO_2$; and heating the composite particle at 650 to 1,200° C.

7. The method for manufacturing an electroconductive particle according to claim 6, wherein the composite particle has an average particle diameter of 30 to 100 nm.

8. The method for manufacturing an electroconductive particle for forming an electrode according to claim 6, wherein a volume of the shell-like ceramic covering the precious metal particle is 2 to 40 vol % based on the whole composite particle.

9. A metal paste for forming an electrode, comprising: an electroconductive particle for forming an electrode defined in claim 1; and a solvent.

10. The paste for forming an electrode according to claim 9, wherein an amount of the electroconductive particle mixed is 4 to 40 vol % with respect to the whole paste.

11. An electrode, being made by firing of a paste for forming an electrode, said paste being defined in claim 9.

12. The electroconductive particle for forming an electrode according to claim 2, wherein a volume of the first ceramic particle dispersed in the precious metal particle is 0.5 to 15 vol % based on the whole electroconductive particle.

13. The electroconductive particle for forming an electrode according to claim 2, wherein the precious metal particle is Pt.

14. The electroconductive particle for forming an electrode according to claim 3, wherein the precious metal particle is Pt.

15. The electroconductive particle for forming an electrode according to claim 12, wherein the precious metal particle is Pt.

16. The electroconductive particle for forming an electrode according to claim 2, wherein the precious metal particle is a Pt—Pd alloy containing 30 wt % or less of Pd.

17. The electroconductive particle for forming an electrode according to claim 3, wherein the precious metal particle is a Pt—Pd alloy containing 30 wt % or less of Pd.

18. The electroconductive particle for forming an electrode according to claim 12, wherein the precious metal particle is a Pt—Pd alloy containing 30 wt % or less of Pd.

19. A method for manufacturing an electroconductive particle for forming an electrode, said electroconductive particle defined in claim 2, comprising:
   manufacturing a composite particle having a core/shell structure composed of a precious metal particle comprising Pt or a Pt alloy and a shell-like ceramic covering at least a part of the precious metal particle and comprising $Al_2O_3$ or $ZrO_2$; and heating the composite particle at 650 to 1,200° C.

20. A method for manufacturing an electroconductive particle for forming an electrode, said electroconductive particle defined in claim 3, comprising:
   manufacturing a composite particle having a core/shell structure composed of a precious metal particle comprising Pt or a Pt alloy and a shell-like ceramic covering at least a part of the precious metal particle and comprising $Al_2O_3$ or $ZrO_2$; and heating the composite particle at 650 to 1,200° C.

* * * * *